US012735510B2

(12) United States Patent
Li et al.

(10) Patent No.: US 12,735,510 B2
(45) Date of Patent: Sep. 15, 2026

(54) **METHOD FOR PURIFYING *FOMES OFFICINALIS* POLYSACCHARIDE BY SEQUENTIAL SIMULATED MOVING CHROMATOGRAPHY**

(71) Applicants: HEILONGJIANG BAYI AGRICULTURAL UNIVERSITY, Daqing (CN); Heilongjiang Bayi Agricultural University Mudanjiang Institute of Food and Biotechnology, Mudanjiang (CN)

(72) Inventors: Liangyu Li, Daqing (CN); Tianfeng He, Daqing (CN); Rongan Cao, Daqing (CN); Baoxin Lu, Daqing (CN); Chaoyang Li, Daqing (CN); Yuankai Wang, Daqing (CN); Xinmei Lin, Daqing (CN); Rongpeng Bao, Daqing (CN)

(73) Assignees: HEILONGJIANG BAYI AGRICULTURAL UNIVERSITY, Daqing (CN); Heilongjiang Bayi Agricultural University Mudanjiang institute of Food and Biotechnology, Mudanjiang (CN)

( * ) Notice: Subject to any disclaimer, the term of this patent is extended or adjusted under 35 U.S.C. 154(b) by 411 days.

(21) Appl. No.: 18/450,681

(22) Filed: Aug. 16, 2023

(65) Prior Publication Data

US 2024/0218084 A1 Jul. 4, 2024

Related U.S. Application Data

(63) Continuation of application No. PCT/CN2023/097440, filed on May 31, 2023.

(30) Foreign Application Priority Data

Dec. 28, 2022 (CN) ........................ 202211696438.9

(51) Int. Cl.

*C08B 37/00* (2006.01)
*A61K 36/07* (2006.01)
*B01D 15/18* (2006.01)

(52) U.S. Cl.

CPC .......... *C08B 37/0003* (2013.01); *A61K 36/07* (2013.01); *B01D 15/1828* (2013.01); *B01D 15/185* (2013.01); *A61K 2236/39* (2013.01)

(58) Field of Classification Search

CPC ............ C08B 37/0003; A61K 2236/55; A61K 2236/39; A61K 36/07; B01D 15/1828; B01D 15/185

USPC ........................................................ 536/127

See application file for complete search history.

(56) References Cited

FOREIGN PATENT DOCUMENTS

WO WO 2015/049331 A1 * 4/2015 ........... B01D 15/185

OTHER PUBLICATIONS

Zhang, Carbohydrate Polymers, 2022, 295, 1-12.*
Toumi et al, Journal of Chromatography, 2003, 1006, 15-31.*
Na et al, Transactions of the Chinese Society of Agricultural Engineering 2012, 28 (21), 287-292.*

* cited by examiner

*Primary Examiner* — Ganapathy Krishnan
(74) *Attorney, Agent, or Firm* — Pilloff Passino & Cosenza LLP; Rachel Pilloff; Sean Passino

(57) ABSTRACT

A method for purifying a *Fomes officinalis* polysaccharide by sequential simulated moving chromatography is provided by the present application, relating to the technical field of biological extraction. The method includes the following steps: step 1, leaching *Fomes officinalis* to obtain a polysaccharide extractive solution; step 2, purifying the polysaccharide extractive solution by sequential simulated moving chromatography to obtain a purified solution; and step 3, subjecting the purified solution to a treatment of refining and removing impurities, followed by concentrating and drying to obtain the *Fomes officinalis* polysaccharide. The *Fomes officinalis* polysaccharide prepared the method is applied in preparing products for promoting NO production by macrophages.

8 Claims, 2 Drawing Sheets

METHOD FOR PURIFYING *FOMES OFFICINALIS* POLYSACCHARIDE BY SEQUENTIAL SIMULATED MOVING CHROMATOGRAPHY

CROSS-REFERENCE TO RELATED APPLICATIONS

This application is a continuation of PCT/CN2023/097440, filed May 31, 2023 and claims priority of Chinese Patent Application No. 202211696438.9, filed on Dec. 28, 2022, the entire contents of which are incorporated herein by reference.

TECHNICAL FIELD

The present application relates to the technical field of biological extraction, and in particular to a method for purifying a *Fomes officinalis* polysaccharide by sequential simulated moving chromatography.

BACKGROUND

*Fomes officinalis* is a class of fungi of the genus *Phellinus* with medicinal functions, mainly including *Phellinus pini, Fomes fomentarius, Fomitopsis pinicola, Fomitopsis rosea*, and *Laricifomes officinalis*, etc. It is found that polysaccharides of this class of fungi have a significant anticancer effect, and can therefore be used in treating oesophageal cancer, gastric cancer, colon cancer, rectal cancer, lung cancer, breast cancer, uterine cancer, etc., and improve the symptoms of the patients, including increasing appetite and body weight, and alleviating pain, and so on. At present, there are fewer studies on *Fomes officinalis* polysaccharides. Chinese Patent CN101711774A discloses an application of a *Phellinus rimosus* polysaccharide extract in preparing medicines for preventing and controlling tumour metastasis, which is prepared without removing impurities and of a lower purity, but exhibits an obvious ability to activate polymorphonuclear leukocytes and improve their ability to kill tumour cells and thus exert an inhibitory effect on tumour metastasis and postoperative recurrence; Chinese patent CN113181208A discloses an application of extracellular polysaccharide of *Pyropolyporus fomentarius*, the extracellular polysaccharide of *Pyropolyporus fomentarius* is capable of being used in preparing skin wound healing agent, in particular, it is capable of being used in preparing skin burn healing agent; and Chinese Patent CN103254321A discloses a method for extracting and purifying polysaccharides derived from a medicinal fungus, *Phellinus vaninii*, which uses a solvent extraction method that is complicated to operate and has a low product purity. By reviewing the literature, it is obvious that no large-scale research and production of *Fomes officinalis* polysaccharides has been carried out, and with the deepening of the research, significant development of *Fomes officinalis* polysaccharides is bound to be achieved, and the demand and production are expected to increase dramatically, with a promising market prospect.

At present, the method of removing small molecules of polysaccharides mainly adopts the membrane separation method, which has the problems of large investment in equipment, easy to membrane contamination, and the necessity of frequent sterilization and cleaning, and is difficult to be promoted and applied in industry. The method of polysaccharide decolourisation mostly uses $H_2O_2$, with a low efficiency, high solvent consumption and high pollution, not suitable for industrial production. As market competition becomes increasingly intense, the existing technology of polysaccharide decontamination of *Fomes officinalis* can no longer meet the existing technical needs, and there is an urgent need for efficient industrialized polysaccharide decontamination technology.

Sequential simulated moving bed chromatography (SSMB) is an internationally advanced simulated moving bed chromatography separation technology, which has the advantages of small footprint, high feeding concentration, high feeding volume, low eluent dosage, high product purity and yield, and high export concentration over simulated moving bed chromatography (SMB) technology, and has been widely used in related fields abroad; yet, no report on the research of SSMB for the removal of impurities from *Fomes officinalis* polysaccharides has been seen.

SUMMARY

It is an objective of the present application to provide a method for purifying a *Fomes officinalis* polysaccharide by sequential simulated moving chromatography, so as to solve the above problems of the prior art. The method of the present application makes it possible to improve both the impurity removal rate and the yield of *Fomes officinalis* polysaccharides, and thus to be capable of significantly improving the quality of the product.

In order to achieve the above objectives, the present application provides following technical schemes:

the present application provides a method for purifying a *Fomes officinalis* polysaccharide by sequential simulated moving chromatography, including following steps:

step 1, leaching *Fomes officinalis* to obtain a polysaccharide extractive solution;

step 2, purifying the polysaccharide extractive solution by sequential simulated moving chromatography to obtain a purified solution; and step 3, subjecting the purified solution to a treatment of refining and removing impurities, followed by concentrating and drying to obtain the *Fomes officinalis* polysaccharide;

in the step 2, the sequential simulated moving chromatography includes six chromatography columns, numbered columns 1-6; column 1 is configured with a feeding inlet, an eluent inlet, a discharge outlet and an impurity component outlet; column 2, column 3 and column 6 are configured with a feeding inlet and a discharge outlet respectively; column 4 is configured with a feeding inlet, a polysaccharide raw material inlet and a discharge outlet; column 5 is configured with a feeding inlet, a discharge outlet and a polysaccharide component outlet; the discharge outlet of column 1 is connected with the feeding inlet of the column 2, the discharge outlet of column 2 is connected with the feeding inlet of the column 3, the discharge outlet of column 3 is connected with the feeding inlet of the column 4, the discharge outlet of column 4 is connected with the feeding inlet of the column 5, the discharge outlet of column 5 is connected with the feeding inlet of the column 6, and finally the discharge outlet of column 6 is connected with the feeding inlet of the column 1 to form a closed loop.

Optionally, in the step 1, the *Fomes officinalis* is one or more of *Phellinus pini, Fomes fomentarius, Fomitopsis pinicola, Fomitopsis rosea*, and *Laricifomes officinalis*.

Optionally, in the step 2, a concentration of the polysaccharide extractive solution is 10-20 weight percentage (wt %).

Optionally, in the step 2, steps of the purifying include:

step a, opening the impurity component outlet of the column 1 and the polysaccharide component outlet of the column 5, introducing eluent from the eluent inlet of the column 1, and discharging impurity components from the impurity component outlet of the column 1; while introducing eluent from the eluent inlet of the column 1, introducing the polysaccharide extractive solution from the polysaccharide raw material inlet of the column 4, and discharging a first part of polysaccharide component through the polysaccharide component outlet of the column 5;

step b, closing the eluent inlet of the column 1, the impurity component outlet of the column 1, the polysaccharide raw material inlet of the column 4 and the polysaccharide component outlet of the column 5, where material does not flow in or out, a large circulation is carried out and a liquid flow direction is from the column 1 to the column 6; and step c, opening the eluent inlet of the column 1 and the polysaccharide component outlet of the column 5, introducing eluent from the eluent inlet of the column 1, and discharging a second part of polysaccharide component from the polysaccharide component outlet of the column 5.

Optionally, in the step a, an amount of the eluent is 10-30% of a volume of a single column chromatography column, and a feeding amount of the polysaccharide extractive solution is 5-10% of the volume of the single column chromatography column; in the step b, a circulation amount of the large circulation is 20-40% of the volume of the single column chromatography column; and in the step c, an amount of the eluent is 5-20% of the volume of the single column chromatography column.

Optionally, in the step 2, a stationary phase of the chromatography column is a strongly acidic hydrogen ion resin.

Optionally, in the step 2, a working temperature of the purifying is in a range of 50-70 degrees Celsius (° C.).

Optionally, in the step 3, the treatment of refining and removing impurities adopts a method of column chromatography decolorisation, and a macroporous resin for the column chromatography decolorisation is AB-8, X-5 or ADS-4.

The present application also provides a *Fomes officinalis* polysaccharide prepared by the method for purifying a *Fomes officinalis* polysaccharide by sequential simulated moving chromatography.

The present application also provides an application of the *Fomes officinalis* polysaccharide in preparing products for promoting NO production by macrophages.

The present application discloses the following technical effects:

the present application provides a method for purifying the *Fomes officinalis* polysaccharide, with low process operation cost, and the impurity removal rate and yield of the *Fomes officinalis* polysaccharide are significantly improved, with the impurity removal rate reaching 80-90%, the yield reaching 80-90%, and the decolourisation rate reaching 60%-80%; the method according to the present application is non-polluting, with low subsequent costs, simplified operation steps, simple equipment, reduced equipment investment, increased resin utilisation, and capable of continuous production with improved production efficiency.

BRIEF DESCRIPTION OF THE DRAWINGS

For a clearer description of the technical schemes in the embodiments or prior art of the present application, the accompanying drawings to be used in the embodiments are briefly described hereinafter, and it is obvious that the accompanying drawings in the description hereinafter are only some of the embodiments of the present application, and that for a person of ordinary skill in the field, other accompanying drawings are available on the basis of the accompanying drawings without any creative labor.

DETAILED DESCRIPTION OF THE EMBODIMENTS

Various exemplary embodiments of the present application are now described in detail, and this detailed description should not be considered as a limitation of the present application, but should be understood as a further detailed description of certain aspects, features, and embodiments of the present application.

It should be understood that the terminology described in the present application is only for describing specific embodiments and is not used to limit the present application. In addition, for the numerical range in the present application, it should be understood that each intermediate value between the upper limit and the lower limit of the range is also specifically disclosed. Intermediate values within any stated value or stated range, as well as each smaller range between any other stated value or intermediate values within the stated range are also included in the present application. The upper and lower limits of these smaller ranges can be independently included or excluded from the range.

Unless otherwise specified, all technical and scientific terms used herein have the same meaning as commonly understood by one of ordinary skill in the art to which this application relates. Although the present application only describes the preferred methods and materials, any methods and materials similar or equivalent to those described herein may also be used in the practice or testing of the present application. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present application without departing from the scope or spirit of the present application. Other embodiments will be apparent to the skilled person from the description of the application. The description and example of that present application are exemplary only.

The terms “comprising”. “including”, “having” and “containing” used in this specification are all open terms, which means including but not limited to.

Figure 2:
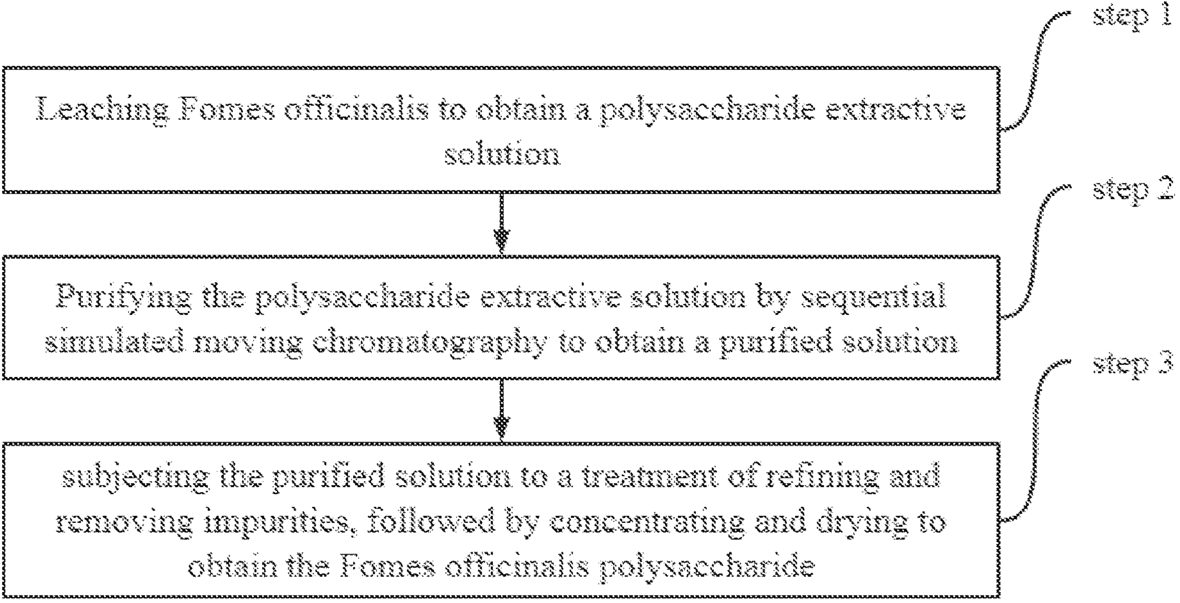
FIG. 2 shows a process of a method for purifying a *Fomes officinalis* polysaccharide by sequential simulated moving chromatography according to the present application.

As shown in FIG. 2, a method for purifying a *Fomes officinalis* polysaccharide by sequential simulated moving chromatography, including following steps:

step 1, leaching *Fomes officinalis* to obtain a polysaccharide extractive solution;

step 2, purifying the polysaccharide extractive solution by sequential simulated moving chromatography to obtain a purified solution; and step 3, subjecting the purified solution to a treatment of refining and removing impurities, followed by concentrating and drying to obtain the *Fomes officinalis* polysaccharide.

Figure 1:
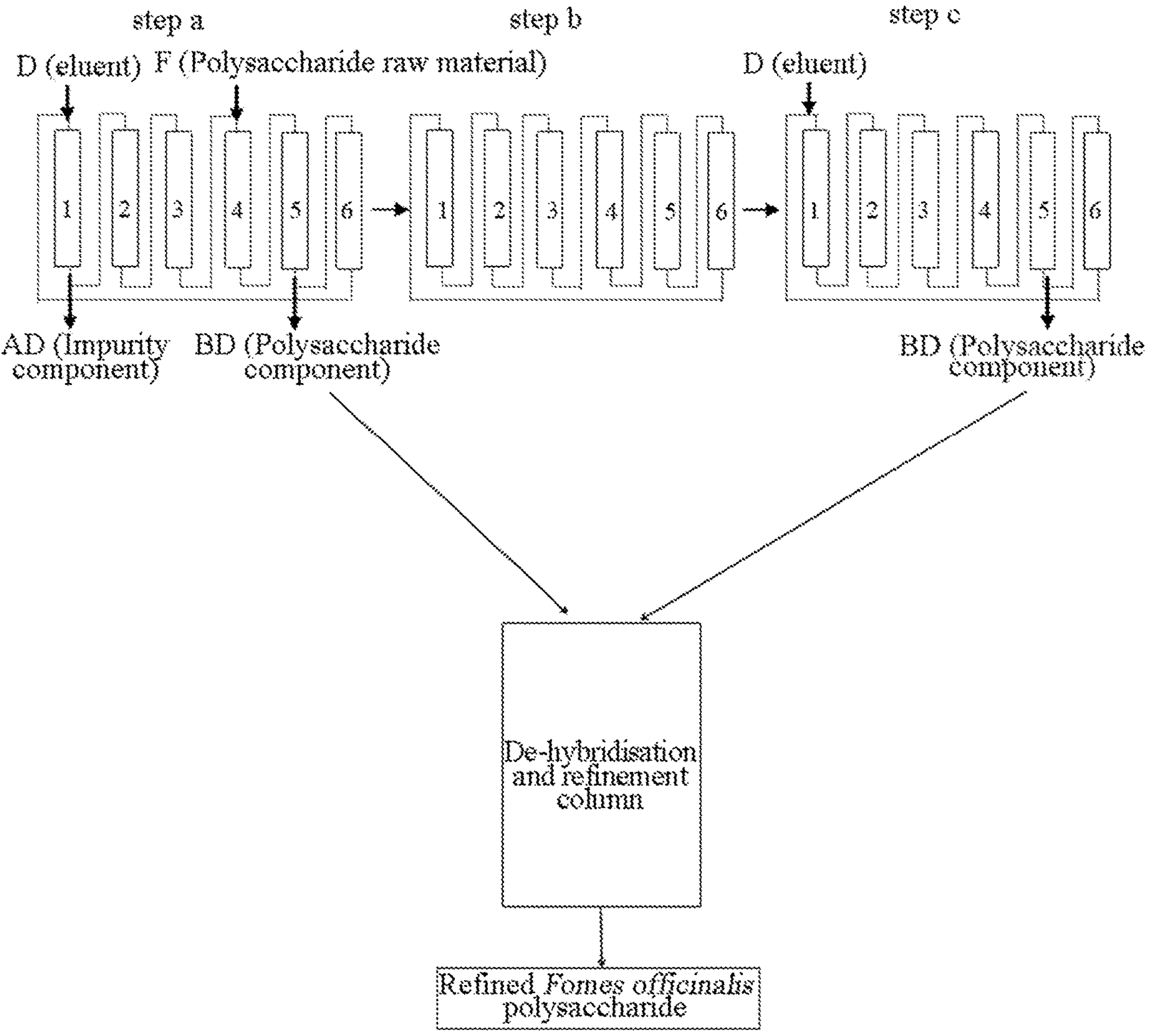
FIG. 1 shows a process of sequential simulated moving chromatography purification of the present application.

As shown in FIG. 1, the sequential simulated moving chromatography used in the following embodiments includes six columns (35 millimeters (mm) in inner diameter and 1,000 mm in length), numbered columns 1-6, each column is 1 Liter (L) in volume, totaling 6 L, and the feeding and discharging are controlled by solenoid valves; column 1 is configured with a feeding inlet, an eluent inlet, a discharge outlet and an impurity component outlet; column 2, column 3 and column 6 are configured with a feeding inlet and a discharge outlet respectively; column 4 is configured with a feeding inlet, a polysaccharide raw material inlet and a discharge outlet; column 5 is configured with a feeding inlet, a discharge outlet and a polysaccharide component outlet; the discharge outlet of column 1 is connected with the feeding inlet of the column 2, the discharge outlet of column 2 is connected with the feeding inlet of the column 3, the discharge outlet of column 3 is connected with the feeding inlet of the column 4, the discharge outlet of column 4 is connected with the feeding inlet of the column 5, the discharge outlet of column 5 is connected with the feeding inlet of the column 6, and finally the discharge outlet of column 6 is connected with the feeding inlet of the column 1 to form a closed loop. The de-hybridisation and refinement column is a single column (100 mm in inner diameter and 1000 mm in length), with feeding and discharge controlled by a solenoid valve.

The *Fomes officinalis* of the present application includes one or more of *Phellinus pini, Fomes fomentarius, Fomitopsis pinicola, Fomitopsis rosea*, and *Laricifomes officinalis*, and a method for purifying a *Fomes officinalis* polysaccharide by sequential simulated moving chromatography is described below by taking *Phellinus pini* as an example.

A method for preparing a polysaccharide extractive solution used in the following embodiments includes: *Phellinus pini* is crushed into powder, then defatted with petroleum ether, and then the defatted *Phellinus pini* powder is added to deionized water (the mass ratio of defatted *Phellinus pini* powder to deionized water is 1:15), after which ultrasonic extraction is carried out, with ultrasonic power of 300 Watts (W), ultrasonic temperature of 40 degrees Celsius (° C.), ultrasonic duration of 20 minutes (min), then anhydrous ethanol is added to make the final mass concentration of ethanol of 80%, and the alcohol precipitation is carried out to remove protein to obtain the polysaccharide extractive solution.

Embodiment 1

(1) Preparation of polysaccharide extractive solution

The polysaccharide extract is blended to a concentration of 10 weight percentage (wt %) using deionized water.

(2) Simulated moving chromatography purification

In this step, the stationary phase is strong acidic hydrogen ion resin 99 $H^+$320, and the working temperature is 50° C. As shown in FIG. 1, the following operations are carried out:

step a, opening the impurity component outlet of column 1 and the polysaccharide component outlet of column 5, and simultaneously feeding polysaccharide extractive solution and eluent, namely, feeding eluent D (deionized water) from the eluent inlet of the column 1, and discharging component AD (impurity component) from the impurity component outlet of the column 1; while introducing eluent from the eluent inlet of the column 1, introducing the polysaccharide extractive solution from the polysaccharide raw material inlet of the column 4, and discharging a first part of component BD (first part of polysaccharide component) through the polysaccharide component outlet of the column 5, where the amount of the eluent is 136.88 milliliters (mL) and the amount of the polysaccharide extractive solution is 85.26 mL;

step b, closing the eluent inlet of the column 1, the impurity component outlet of the column 1, the polysaccharide raw material inlet of the column 4 and the polysaccharide component outlet of the column 5, where the material does not flow in or out, a large circulation is carried out and a liquid flow direction is from the column 1 to the column 6; and the circulation amount is 273.00 mL; and step c, opening the eluent inlet of the column 1 and the polysaccharide component outlet of the column 5, introducing eluent from the eluent inlet of the column 1, and discharging a another part of component BD (second part of polysaccharide component) from the polysaccharide component outlet of the column 5, where the amount of the eluent is 168.74 mL.

Once the operation of column 1 is finished, the above three steps are repeated in sequence, and the feeding and discharging positions are moved to the next column along the direction of columns 1 to 6, and this procedure is followed in all subsequent operations.

(3) The polysaccharide components (i.e., purified solution) obtained from step a and step c in step 2 are combined and transferred to a transfer tank, after which they are pumped into a refining chromatography column, and adsorption and decolourisation are carried out using an AB-8 macroporous resin, with an up-sampling volume of 2 bed volume (BV) and a flow rate of 2 bed volume per hour (BV/h), to obtain the refined and purified solution, which is then concentrated in vacuum (at a concentration temperature of 45° C.), and then subjected to freeze-drying to obtain the *Fomes officinalis* polysaccharide. It should be noted that the adsorption is followed by elution using 60% volume fraction of ethanol solution with an elution volume of 2 BV and a flow rate of 1 BV/h; and finally, regeneration is carried out using deionized water with an elution volume of 3 BV and a flow rate of 2 BV/h. After regeneration, the feeding is repeated to achieve the effect of decolourisation by column chromatography.

The *Fomes officinalis* polysaccharide prepared in this embodiment shows a removal rate of 82.6%, a yield of 83.2%, a decolourisation rate of 75.6% and a purity of 76.8%.

Embodiment 2

(1) Preparation of polysaccharide extractive solution

The polysaccharide extract is blended to a concentration of 15 wt % using deionized water.

(2) Simulated moving chromatography purification

In this step, the stationary phase is strong acidic hydrogen ion resin 106 $H^+$, and the working temperature is 65° C. As shown in FIG. 1, the following operations are carried out:

step a, opening the impurity component outlet of column 1 and the polysaccharide component outlet of column 5, and simultaneously feeding polysaccharide extractive solution and eluent, namely, feeding eluent D (deionized water) from the eluent inlet of the column 1, and discharging component AD (impurity component) from the impurity component outlet of the column 1; while introducing eluent from the eluent inlet of the column 1, introducing the polysaccharide extractive solution from the polysaccharide raw material inlet of the column 4, and discharging a first part of component BD (first part of polysaccharide component) through the polysaccharide component outlet of the column 5, where the amount of the eluent is 146.27 mL and the amount of the polysaccharide extractive solution is 106.25 mL;

step b, closing the eluent inlet of the column 1, the impurity component outlet of the column 1, the polysaccharide raw material inlet of the column 4 and the polysaccharide component outlet of the column 5, where the material does not flow in or out, a large circulation is carried out and a liquid flow direction is from the column 1 to the column 6; and the circulation amount is 265.00 mL; and step c, opening the eluent inlet of the column 1 and the polysaccharide component outlet of the column 5, introducing eluent from the eluent inlet of the column 1, and discharging a another part of component BD (second part of polysaccharide component) from the polysaccharide component outlet of the column 5, where the amount of the eluent is 168.63 mL.

Once the operation of column 1 is finished, the above three steps are repeated in sequence, and the feeding and discharging positions are moved to the next column along the direction of columns 1 to 6, and this procedure is followed in all subsequent operations.

(3) The polysaccharide components (i.e., purified solution) obtained from step a and step c in step 2 are combined and transferred to a transfer tank, after which they are pumped into a refining chromatography column, and adsorption and decolourisation are carried out using an X-5 macroporous resin, with an up-sampling volume of 2 BV and a flow rate of 2.5 BV/h, to obtain the refined and purified solution, which is then concentrated in vacuum (at a concentration temperature of 45° C.), and then subjected to freeze-drying to obtain the *Fomes officinalis* polysaccharide. It should be noted that the adsorption is followed by elution using 70% volume fraction of ethanol solution with an elution volume of 2.5 BV and a flow rate of 1.5 BV/h; and finally, regeneration is carried out using deionized water with an elution volume of 4 BV and a flow rate of 3 BV/h. After regeneration, the feeding is repeated to achieve the effect of decolourisation by column chromatography.

The *Fomes officinalis* polysaccharide prepared in this embodiment shows a removal rate of 86.7%, a yield of 81.7%, a decolourisation rate of 78.4% and a purity of 79.2%.

Embodiment 3

(1) Preparation of polysaccharide extractive solution

The polysaccharide extract is blended to a concentration of 20 wt % using deionized water.

(2) Simulated moving chromatography purification

In this step, the stationary phase is strong acidic hydrogen ion resin 99 $H^+$320, and the working temperature is 70° C. As shown in FIG. 1, the following operations are carried out:

step a, opening the impurity component outlet of column 1 and the polysaccharide component outlet of column 5, and simultaneously feeding polysaccharide extractive solution and eluent, namely, feeding eluent D (deionized water) from the eluent inlet of the column 1, and discharging component AD (impurity component) from the impurity component outlet of the column 1; while introducing eluent from the eluent inlet of the column 1, introducing the polysaccharide extractive solution from the polysaccharide raw material inlet of the column 4, and discharging a first part of component BD (first part of polysaccharide component) through the polysaccharide component outlet of the column 5, where the amount of the eluent is 168.54 mL and the amount of the polysaccharide extractive solution is 110.35 mL;

step b, closing the eluent inlet of the column 1, the impurity component outlet of the column 1, the polysaccharide raw material inlet of the column 4 and the polysaccharide component outlet of the column 5, where the material does not flow in or out, a large circulation is carried out and a liquid flow direction is from the column 1 to the column 6; and the circulation amount is 315.00 mL; and step c, opening the eluent inlet of the column 1 and the polysaccharide component outlet of the column 5, introducing eluent from the eluent inlet of the column 1, and discharging a another part of component BD (second part of polysaccharide component) from the polysaccharide component outlet of the column 5, where the amount of the eluent is 173.56 mL.

Once the operation of column 1 is finished, the above three steps are repeated in sequence, and the feeding and discharging positions are moved to the next column along the direction of columns 1 to 6, and this procedure is followed in all subsequent operations.

(3) The polysaccharide components (i.e., purified solution) obtained from step a and step c in step 2 are combined and transferred to a transfer tank, after which they are pumped into a refining chromatography column, and adsorption and decolourisation are carried out using an ADS-4 macroporous resin, with an up-sampling volume of 5 BV and a flow rate of 3 BV/h, to obtain the refined and purified solution, which is then concentrated in vacuum (at a concentration temperature of 45° C.), and then subjected to freeze-drying to obtain the *Fomes officinalis* polysaccharide. It should be noted that the adsorption is followed by elution using 90% volume fraction of ethanol solution with an elution volume of 3 BV and a flow rate of 2 BV/h; and finally, regeneration is carried out using deionized water with an elution volume of 5 BV and a flow rate of 5 BV/h. After regeneration, the feeding is repeated to achieve the effect of decolourisation by column chromatography.

The *Fomes officinalis* polysaccharide prepared in this embodiment shows a removal rate of 87.3%, a yield of 81.7%, a decolourisation rate of 66.7% and a purity of 79.8%.

Effect Description:

Macrophage RAW264.7 is stimulated using *Fomes officinalis* polysaccharides prepared in Embodiments 1-3, and the concentrations of NO produced therefrom are determined, and the results are shown in Table 1.

Specific experimental methods: 100 microliters (L) of RAW264.7 cells ($1\times10^6$ cells/mL) are added to 96 microtiter plates and pre-cultured in a 37° C. 5% $CO_2$ incubator for 24 hours (h). The supernatant is discarded, and 200 μL of 5 micrograms per milliliter (μg/mL) polysaccharide solution is added to the cells, the culture solution is used as a negative control, and 1 μg/mL lipopolysaccharide (LPS) is used as a positive control, then the cells are incubated for 24 h. To determine the NO level in the supernatant, 100 μL of supernatant is added with 100 μL of Griess reagent, and the absorbance is measured at 540 nm after 10 min of reaction at room temperature and protected from light using an enzyme labeler (Biotek instruments, Winooski, VT, USA), and the NO yield is calculated by substituting the absorbance value of the samples into the standard curve, using sodium nitrite as the standard.

TABLE 1

| Embodiments | NO yield |
|---|---|
| Embodiment 1 | 37.33 μmol/L |
| Embodiment 2 | 39.56 μmol/L |
| Embodiment 3 | 40.62 μmol/L |
| Positive control group | 41.06 μmol/L |

The above-mentioned embodiments only describe the preferred mode of the present application, and do not limit the scope of the present application. Under the premise of not departing from the design spirit of the application, various modifications and improvements made by ordinary technicians in the field to the technical scheme of the present application shall fall within the protection scope determined by the claims of the present application.

What is claimed is:

1. A method for purifying a *Fomes officinalis* polysaccharide by sequential simulated moving chromatography, comprising the following steps:

step 1, leaching *Fomes officinalis* to obtain a polysaccharide extractive solution;

step 2, purifying the polysaccharide extractive solution by sequential simulated moving chromatography to obtain a purified solution; and step 3, subjecting the purified solution to a treatment of refining and removing impurities, followed by concentrating and drying to obtain the *Fomes officinalis* polysaccharide;

wherein in the step 2, the sequential simulated moving chromatography comprises six chromatography columns, numbered columns 1-6; column 1 is configured with a feeding inlet, an eluent inlet, a discharge outlet and an impurity component outlet; column 2, column 3 and column 6 are configured with a feeding inlet and a discharge outlet; column 4 is configured with a feeding inlet, a polysaccharide raw material inlet and a discharge outlet; column 5 is configured with a feeding inlet, a discharge outlet and a polysaccharide component outlet; the discharge outlet of column 1 is connected with the feeding inlet of the column 2, the discharge outlet of column 2 is connected with the feeding inlet of the column 3, the discharge outlet of column 3 is connected with the feeding inlet of the column 4, the discharge outlet of column 4 is connected with the feeding inlet of the column 5, the discharge outlet of column 5 is connected with the feeding inlet of the column 6, and finally the discharge outlet of column 6 is connected with the feeding inlet of the column 1 to form a closed loop.

2. The method for purifying the *Fomes officinalis* polysaccharide by sequential simulated moving chromatography according to claim 1, wherein in the step 1, the *Fomes officinalis* is selected from the group consisting of *Phellinus pini, Fomes fomentarius, Fomitopsis pinicola, Fomitopsis rosea*, and *Laricifomes officinalis.*

3. The method for purifying the *Fomes officinalis* polysaccharide by sequential simulated moving chromatography according to claim 1, wherein in the step 2, a concentration of the polysaccharide extractive solution is 10-20 weight percentage.

4. The method for purifying the *Fomes officinalis* polysaccharide by sequential simulated moving chromatography according to claim 1, wherein in the step 2, steps of the purifying comprise:

step a, opening the impurity component outlet of the column 1 and the polysaccharide component outlet of the column 5, introducing eluent from the eluent inlet of the column 1, and discharging impurity components from the impurity component outlet of the column 1;

while introducing eluent from the eluent inlet of the column 1, introducing the polysaccharide extractive solution from the polysaccharide raw material inlet of the column 4, and discharging a first part of polysaccharide component through the polysaccharide component outlet of the column 5;

step b, closing the eluent inlet of the column 1, the impurity component outlet of the column 1, the polysaccharide raw material inlet of the column 4 and the polysaccharide component outlet of the column 5, where material does not flow in or out, a large circulation is carried out and a liquid flow direction is from the column 1 to the column 6; and step c, opening the eluent inlet of the column 1 and the polysaccharide component outlet of the column 5, introducing eluent from the eluent inlet of the column 1, and discharging a second part of polysaccharide component from the polysaccharide component outlet of the column 5.

5. The method for purifying the *Fomes officinalis* polysaccharide by sequential simulated moving chromatography according to claim 4, wherein in the step a, an amount of the eluent is 10-30% of a volume of a single column chromatography column, and a feeding amount of the polysaccharide extractive solution is 5-10% of the volume of the single column chromatography column; in the step b, a circulation amount of the large circulation is 20-40% of the volume of the single column chromatography column; and in the step c, an amount of the eluent is 5-20% of the volume of the single column chromatography column.

6. The method for purifying the *Fomes officinalis* polysaccharide by sequential simulated moving chromatography according to claim 1, wherein in the step 2, a stationary phase of the chromatography column is a strongly acidic hydrogen ion resin.

7. The method for purifying the *Fomes officinalis* polysaccharide by sequential simulated moving chromatography according to claim 1, wherein in the step 2, a working temperature of the purifying is in a range of 50-70 degrees Celsius.

8. The method for purifying the *Fomes officinalis* polysaccharide by sequential simulated moving chromatography according to claim 1, wherein in the step 3, the treatment of refining and removing impurities adopts a method of column chromatography decolorisation, and a macroporous resin for the column chromatography decolorisation is AB-8, X-5 or ADS-4.

* * * * *